(12) United States Patent
Wang et al.

(10) Patent No.: US 9,083,048 B2
(45) Date of Patent: Jul. 14, 2015

(54) CARBON MONOFLUORIDE IMPREGNATED CURRENT COLLECTOR INCLUDING A 3D FRAMEWORK

(75) Inventors: Francis Wang, Minneapolis, MN (US); Lisa B. Schmalhurst, Bellevue, WA (US); Joseph E. Sunstrom, Newark, DE (US); Ignacio Chi, Mahtomedi, MN (US); Steven P. Findell, New Brighton, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 765 days.

(21) Appl. No.: 13/205,757

(22) Filed: Aug. 9, 2011

(65) Prior Publication Data
US 2012/0078317 A1    Mar. 29, 2012

Related U.S. Application Data

(60) Provisional application No. 61/373,086, filed on Aug. 12, 2010.

(51) Int. Cl.
*H01M 4/66* (2006.01)
*H01M 2/22* (2006.01)
(Continued)

(52) U.S. Cl.
CPC ............ *H01M 4/661* (2013.01); *H01M 2/22* (2013.01); *H01M 2/266* (2013.01); *H01M 4/043* (2013.01); *H01M 4/0478* (2013.01); *H01M 4/133* (2013.01); *H01M 4/1393* (2013.01); *H01M 4/5835* (2013.01); *H01M 4/762* (2013.01);
(Continued)

(58) Field of Classification Search
CPC .................................................. H01M 4/043

USPC .................. 429/162, 144, 254, 219, 224, 241
See application file for complete search history.

(56) References Cited

U.S. PATENT DOCUMENTS

| 4,217,939 A | 8/1980 | Yanagihara et al. |
| 4,791,791 A | 12/1988 | Flegal et al. |

(Continued)

FOREIGN PATENT DOCUMENTS

| EP | 1243680 A2 | 9/2002 |
| EP | 1555244 A2 | 7/2005 |

OTHER PUBLICATIONS

"U.S. Appl. No. 13/205,772, Final Office Action mailed Feb. 19, 2014", 21 pgs.

(Continued)

*Primary Examiner* — Patrick Ryan
*Assistant Examiner* — Alex Usyatinsky
(74) *Attorney, Agent, or Firm* — Schwegman Lundberg & Woessner, P.A.

(57) ABSTRACT

One example includes a battery case sealed to retain electrolyte, an electrode disposed in the battery case, the electrode comprising a current collector formed of a framework defining open areas disposed along three axes ("framework"), the framework electrically conductive, with active material disposed in the open areas; a conductor electrically coupled to the electrode and sealingly extending through the battery case to a terminal disposed on an exterior of the battery case, a further electrode disposed in the battery case, a separator disposed between the electrode and the further electrode and a further terminal disposed on the exterior of the battery case and in electrical communication with the further electrode, with the terminal and the further terminal electrically isolated from one another.

19 Claims, 11 Drawing Sheets

(51) Int. Cl.
*H01M 2/26* (2006.01)
*H01M 4/04* (2006.01)
*H01M 4/133* (2010.01)
*H01M 4/1393* (2010.01)
*H01M 4/583* (2010.01)
*H01M 4/76* (2006.01)
*A61N 1/378* (2006.01)

(52) U.S. Cl.
CPC .............. *A61N1/378* (2013.01); *H01M 2220/30* (2013.01); *Y02E 60/122* (2013.01); *Y10T 29/4911* (2015.01)

(56) References Cited

U.S. PATENT DOCUMENTS

| | | | |
|---|---|---|---|
| 5,116,592 A | 5/1992 | Weinberg | |
| 5,512,390 A | 4/1996 | Obushenko | |
| 5,589,301 A | 12/1996 | Edgington et al. | |
| 5,728,490 A | 3/1998 | Edgington et al. | |
| 5,738,907 A | 4/1998 | Vaccaro et al. | |
| 5,798,033 A | 8/1998 | Uemiya et al. | |
| 6,068,921 A | 5/2000 | Yamana et al. | |
| 6,498,951 B1 * | 12/2002 | Larson et al. | 607/36 |
| 6,605,390 B1 | 8/2003 | Moore et al. | |
| 6,645,667 B1 | 11/2003 | Iwamoto et al. | |
| 6,783,888 B2 | 8/2004 | Gan et al. | |
| 6,979,513 B2 | 12/2005 | Kelley et al. | |
| 7,060,391 B2 | 6/2006 | Gyenge et al. | |
| 7,341,806 B2 | 3/2008 | Kelley et al. | |
| 7,377,948 B2 | 5/2008 | Faris | |
| 7,563,542 B2 | 7/2009 | Yazami et al. | |
| 2001/0020319 A1 | 9/2001 | Farahmandi et al. | |
| 2003/0036001 A1 | 2/2003 | James et al. | |
| 2006/0166078 A1 | 7/2006 | Chen et al. | |
| 2007/0156197 A1 | 7/2007 | Root et al. | |
| 2007/0248887 A1 | 10/2007 | Eskra et al. | |
| 2010/0055571 A1 | 3/2010 | Le Guenne et al. | |
| 2010/0259866 A1 | 10/2010 | Shaffer et al. | |
| 2010/0323244 A1 | 12/2010 | Chiang et al. | |
| 2011/0005065 A1 | 1/2011 | Chiang et al. | |
| 2011/0033747 A1 | 2/2011 | Phillips et al. | |
| 2011/0052994 A1 | 3/2011 | Harada et al. | |
| 2011/0111303 A1 | 5/2011 | Kung et al. | |
| 2012/0041507 A1 | 2/2012 | Wang et al. | |
| 2013/0065122 A1 * | 3/2013 | Chiang et al. | 429/211 |

OTHER PUBLICATIONS

"U.S. Appl. No. 13/205,772, Non Final Office Action mailed Aug. 13, 2013", 19 pgs.
"U.S. Appl. No. 13/205,772, Response filed May 19, 2014 to Final Office Action mailed Feb. 19, 2014", 11 pgs.
"U.S. Appl. No. 13/205,772, Response filed Dec. 11, 2013 to Non Final Office Action mailed Aug. 13, 2013", 12 pgs.
"U.S. Appl. No. 13/205,772, Response filed to Restriction Requirement mailed May 16, 2013", 6 pgs.
"U.S. Appl. No. 13/205,772, Restriction Requirement mailed May 16, 2013", 6 pgs.

* cited by examiner

CARBON MONOFLUORIDE IMPREGNATED CURRENT COLLECTOR INCLUDING A 3D FRAMEWORK

CROSS-REFERENCE TO RELATED APPLICATIONS

This application claims the benefit of U.S. Provisional Application No. 61/373,086, filed on Aug. 12, 2010, under 35 U.S.C. §119(e), which is incorporated herein by reference in its entirety.

TECHNICAL FIELD

This document relates generally to energy storage and particularly to a carbon monofluoride ($CF_x$) impregnated foam current collector.

BACKGROUND

Some electrochemically active battery materials offer superior energy density, but are difficult to implement in a battery using traditional battery manufacturing structures and materials. Specifically, some battery manufacturing structures and methods can render certain battery chemistries less effective. Structures and methods that enable using new battery chemistries would be beneficial.

SUMMARY

A first example includes a battery case sealed to retain electrolyte, an electrode disposed in the battery case, the electrode including a current collector formed of a framework defining open areas disposed along three axes ("framework"), the framework electrically conductive, with active material disposed in the open areas, a conductor electrically coupled to the electrode and sealingly extending through the battery case to a terminal disposed on an exterior of the battery case, a further electrode disposed in the battery case, a separator disposed between the electrode and the further electrode, and a further terminal disposed on the exterior of the battery case and in electrical communication with the further electrode, with the terminal and the further terminal electrically isolated from one another.

Example 2 includes the subject matter of example 1, wherein the framework is formed of a compressed metallic foam defining open areas.

Example 3 includes the subject matter of examples 2, wherein the metallic foam is formed of at least one of the group including aluminum, titanium and stainless steel.

Example 4 includes the subject matter of any of examples 1-3, wherein the active material includes, but it not limited to, carbon monofluoride, with a formula CFx.

Example 5 includes the subject matter of example 4, wherein the electrode has a porosity of from around 30-55% porous.

Example 6 includes the subject matter of any of examples 1-5, wherein the electrode is disposed in a stack of electrodes.

Example 7 includes the subject matter of example 6, wherein the stack of electrodes includes a further electrode including a current collector formed of a compressed framework that is electrically conductive.

Example 8 includes the subject matter of example 7, wherein the stack is formed by a process including stacking an uncompressed electrode and a further uncompressed electrode into an uncompressed stack, and stacking the uncompressed stack.

Example 9 includes the subject matter of any of examples 1-8, wherein the stack is a stack of compressed electrodes, each adapted to stack into the stack.

Example 10 includes a hermetically sealed device housing, a battery disposed in the hermetically sealed device housing, the battery including a battery case sealed to retain electrolyte, an electrode disposed in the battery case, the electrode including a current collector formed of a compressed framework defining open areas disposed along three axes ("framework"), with active material disposed in the open areas, a conductor electrically coupled to the electrode and sealingly extending through the battery case to a terminal disposed on an exterior of the battery case, a further electrode disposed in the battery case, a separator disposed between the electrode and the further electrode, and a further terminal disposed on the exterior of the battery case and in electrical communication with the further electrode, with the terminal and the further terminal electrically isolated from one another, and an electronic cardiac rhythm management circuit coupled to the battery and adapted to discharge the battery to provide a therapeutic pulse.

Example 11 system of claim 10, wherein the device housing has a form factor, and the battery case is shaped to at least partially conform to the form factor.

Example 12 system of claim 11, wherein the battery case has a case shape, and the electrode has an electrode form factor shaped to at least partially mate the case shape.

Example 13 includes disposing active material into a current collector including a framework defining open areas disposed along three axes ("framework"), curing the active material to the current collector, compressing the framework into a shaped electrode, stacking the shaped electrode into a battery stack with other electrodes, disposing the battery stack in a battery case, connecting the electrodes of the battery stack to terminals for coupling to electronics, filling the battery case with electrolyte, and sealing the battery case.

Example 14 includes the subject matter of example 13, further including forming the framework out of a metallic foam.

Example 15 includes the subject matter of any of examples 13-14, further including forming the active material by mixing active material including, but not limited to, carbon monoflouride, into a slurry with binder and conductive additive.

Example 16 includes the subject matter of example 15, wherein disposing active material includes injecting the active material into the framework.

Example 17 includes the subject matter of example 16, wherein curing the active material includes baking the active material in an oven.

Example 18 includes the subject matter of example 17, wherein compressing the framework includes compressing to a porosity of from around 30% to 40%.

Example 19 includes the subject matter of example 18, further including cutting an excised electrode from the shaped electrode.

Example 20 includes the subject matter of example 19, further including stacking the other electrodes into the stack such that the stack has a predetermined energy density.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof.

The scope of the present invention is defined by the appended claims and their legal equivalents.

BRIEF DESCRIPTION OF THE DRAWINGS

The drawings illustrate generally, by way of example, various examples discussed in the present document. The drawings are for illustrative purposes only and may not be to scale.

DETAILED DESCRIPTION

The following detailed description of the present invention refers to subject matter in the accompanying drawings which show, by way of illustration, specific aspects and examples in which the present subject matter may be practiced. These examples are described in sufficient detail to enable those skilled in the art to practice the present subject matter. References to "an", "one", or "various" examples in this disclosure are not necessarily to the same example, and such references contemplate more than one example. The following detailed description is, therefore, not to be taken in a limiting sense, and the scope is defined only by the appended claims, along with the full scope of legal equivalents to which such claims are entitled.

Examples discussed here relate to electrochemical batteries including lithium. In some examples, the anode (or negative electrode) is formed from lithium. In certain examples, a cathode (or positive electrode) is constructed of a mass formed at least partially of carbon. In some instances, the mass is porous. The mass is formed onto a current collector formed of a framework defining open areas disposed along three axes, (as used herein, a "3D framework"). For example, an opening is bounded by edges defining the opening along three axes. The edges defining the opening define planes enclose the opening on all sides. Some instances relate to a lithium primary battery.

$Li/MnO_2$ battery systems, such as those operating at or around 3.0V, can be improved upon. The present subject matter addresses at least one problem with these battery systems: the energy density of $Li/MnO_2$ batteries is difficult to increase, due to the capacity of $MnO_2$ and its maximum loading level. Loading level refers to the amount of active material per unit area (i.e., $g/cm^2$). $CF_x$ batteries provide an opportunity to improve energy density, but existing $CF_x$ designs have drawbacks.

$CF_x$ chemistry has an energy density of around 1.5 times that of $MnO_2$. However, $CF_x$ electrodes are difficult to process in the form of a coated or pelletized electrode. For example, at the end of the discharge of a $Li/CF_x$ battery, the cathode can expand by as much as two to three times, limiting full utilization of the $CF_x$ energy density.

To address inefficiencies that result from the poor electronic conductivity of $CF_x$, some designs use a high percentage of conductive additives, such as acetylene black carbon, to achieve an acceptable level of electronic conductivity. Some of these designs have a porous (e.g., >50% porous) electrode with poor volumetric capacity as a result of the poor tap density of acetylene black carbon. While increasing the size of current collectors addresses certain aspects of the problem, a size increase is not sufficient, as portions of the current collector still fail to adequately conduct with parts of the electrochemically active area of the $CF_x$. Further, size increases are undesirable in implantable devices, as increased size leads to patient discomfort.

Despite these issues, the $Li/CF_x$ chemistry is desirable. $CF_x$ batteries feature high volumetric capacity. $CF_x$ batteries have desirable long term stability. Some have less than one percent self discharge per year, for example. $CF_x$ batteries have desirable voltage characteristics. Some have an open circuit voltage of around 3.2 volts, for example. Some have a closed circuit voltage of around 2.5 to 2.7 volts, for example. $CF_x$ batteries additionally have predictable low to medium rate performance.

Because $CF_x$ offers these benefits, various examples provide a current collector to combine $CF_x$ with a 3D framework. The 3D framework is electrically conductive. The 3D framework together with active material comprises a cathode in various examples. Various examples provide a 3D framework for the $CF_x$ cathode that addresses the above inefficiencies to provide a $CF_x$ battery that discharges well and has an improved energy density. In certain examples, the 3D framework is porous, but the present subject matter is not so limited. Certain examples include foam. Various examples are metallic. Additional 3D frameworks include fabrics, thatches, braids, scaffolding, skeleton, fins, tendrils and the like. The 3D framework examples disclosed here include features that can be used in combination, that is, aspects from one 3D framework are combinable aspects from another 3D framework, in various examples.

Figure 1:
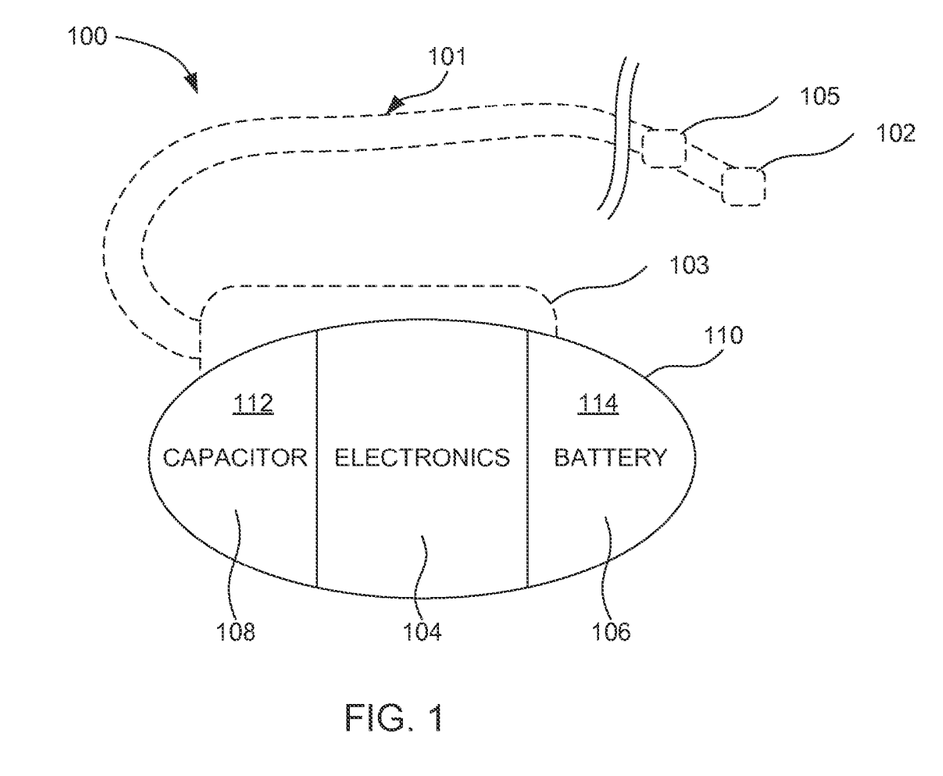
FIG. 1 is a schematic of a medical system including a battery that includes a fluorinated carbon framework defining open areas disposed along three axes, according to some examples.

FIG. 1 is a schematic of a medical system including a battery that includes a 3D framework, according to certain examples. The system 100 represents any number of systems to provide therapeutic stimulus, such as to a heart. Examples of medical systems include, but are not limited to, implantable pacemakers, implantable defibrillators, implantable nerve stimulation devices and devices that provide stimulation from outside the body, including, but not limited to, external defibrillators.

In various examples, electronics 104 are to monitor the patient, such as by monitoring a sensor 105, and to monitor and control activity within the system 100. In some examples, the electronics 104 are to monitor a patient, diagnose a condition to be treated such as an arrhythmia, and control delivery of a stimulation pulse of energy to the patient. In some instances, electronics 104 are powered wirelessly using an inductor. In additional configurations, the electronics 104 are powered by a battery 106. In some examples, electronics 104 are to direct small therapeutic bursts of energy from the battery 106 to a patient.

For therapies that use energy discharge rates exceeding what battery 106 is able to provide, such as defibrillation, a capacitor 108 is used. Energy from the battery 106 is controlled by the electronics 104 to charge the capacitor 108. The capacitor 108 is controlled with the electronics 104 to discharge to a patient to treat the patient. In certain examples, the capacitor 108 completely discharges to a patient, and in additional examples is switched on to provide therapeutic energy and switched off to truncate therapy delivery.

Some instances of a system 100 include an optional lead system 101. In certain instances, after implantation, the lead system 101 or a portion of the lead system 101 is in electrical communication with tissue to be stimulated. For example, some configurations of lead system 101 contact tissue with a stimulation electrode 102. The lead system 101 couples to other portions of the system 100 via a connection in a header 103. Examples of the system 101 use different numbers of stimulation electrodes and/or sensors in accordance with the needs of the therapy to be performed.

Additional examples function without a lead 101 and are leadless. Leadless examples are positioned in contact with the tissue to be stimulated, or are positioned proximal to a tissue to be stimulated to shock the tissue through intermediary tissue. In certain examples, leadless systems are easier to implant and are less expensive as they do not use additional lead components. The housing 110 is used as an electrode in leadless configurations, in certain examples.

In certain examples, the electronics 104 include an electronic cardiac rhythm management circuit coupled to the battery 106 and the capacitor 108 to discharge the capacitor 108 to provide a therapeutic defibrillation pulse. In some instances, the system 100 includes an anode and a second electrode such as a cathode sized to deliver a defibrillation pulse of at least approximately 50 joules. This energy level is predetermined to achieve a delivered energy level mandated by a governing body or standard associated with a geographic region, such as a European country. In an additional example, the anode and second electrode are sized to deliver a defibrillation pulse of at least approximately 60 joules. This energy level is predetermined to achieve an energy level mandated by a governing body of another region, such as the United States. In some instances, electronics 104 are to control discharge of a defibrillation pulse so that the medical system 100 delivers only the energy mandated by the region in which the system 100 is used.

In certain examples, the battery 106 includes a battery case 114 sealed to retain electrolyte. In certain examples, the battery case 114 is welded. In some instances, the battery case 114 is hermetically sealed. In additional examples, the battery case 114 is sealed to retain electrolyte, but is sealed with a seal to allow flow of other matter, such as gaseous diatomic hydrogen or a helium molecule. Some of these examples use an epoxy seal. Several materials can be used to form battery case 114, including, but not limited to, aluminum, titanium, stainless steel, nickel, a polymeric material, or combinations of these materials. The battery case 114 is sealed to retain electrolyte. The battery case 114 includes a seal, such as a resin based seal including but not limited to epoxy, in some examples. Certain examples include a rubber seal to seal multiple case portions to one another, or to seal subcomponents such as a feedthrough to one or more case portions. In certain examples, the battery case 114 is welded together from subcomponents. Some instances include a case that includes one or more backfill ports, but the present subject matter is not so limited.

In certain examples, the capacitor 108 includes a capacitor case 112 sealed to retain electrolyte. In some examples, the capacitor case 112 is welded. In some instances, the capacitor case 112 is hermetically sealed. In additional examples, the capacitor case 112 is sealed to retain electrolyte, but is sealed with a seal to allow flow of other matter, such as gaseous diatomic hydrogen or a helium molecule. Some of these examples use an epoxy seal. Several materials can be used to form capacitor case 112, including, but not limited to, aluminum, titanium, stainless steel, nickel, a polymeric material, or combinations of these materials. The capacitor case 112 is sealed to retain electrolyte. Various electrolytes can be used including, but not limited to, Suzuki-Techno Corporation electrolyte model 1184. The capacitor case 112 includes a seal, such as a resin based seal including but not limited to epoxy, in certain examples. Some instances include a rubber seal to seal multiple case portions to one another, or to seal subcomponents such as a feedthrough to one or more case portion. In some instances, the capacitor case 112 is welded together from subcomponents. Certain examples include a case that includes one or more backfill ports, but the present subject matter is not so limited.

A hermetically sealed device housing 110 is used to house components, such as the battery 106, the electronics 104, and the capacitor 108. Hermeticity is provided by welding components into the hermetically sealed device housing 110 in certain examples. Other examples bond portions of the housing 110 together with an adhesive such as a resin based adhesive such as epoxy. Accordingly, some examples of the housing 110 include an epoxy sealed seam or port. Several materials can be used to form housing 110, including, but not limited to, titanium, stainless steel, nickel, a polymeric material, or combinations of these materials. In various examples, the housing 110 and the case 112 are biocompatible.

The battery 106 is improved by the present electrode technology in part because it can be made smaller. In certain examples, it is manufacturable with less expense. The improvement provided by these electrodes is pertinent to any application where high-energy, high-voltage, or space-efficient batteries are desirable.

Figure 2:
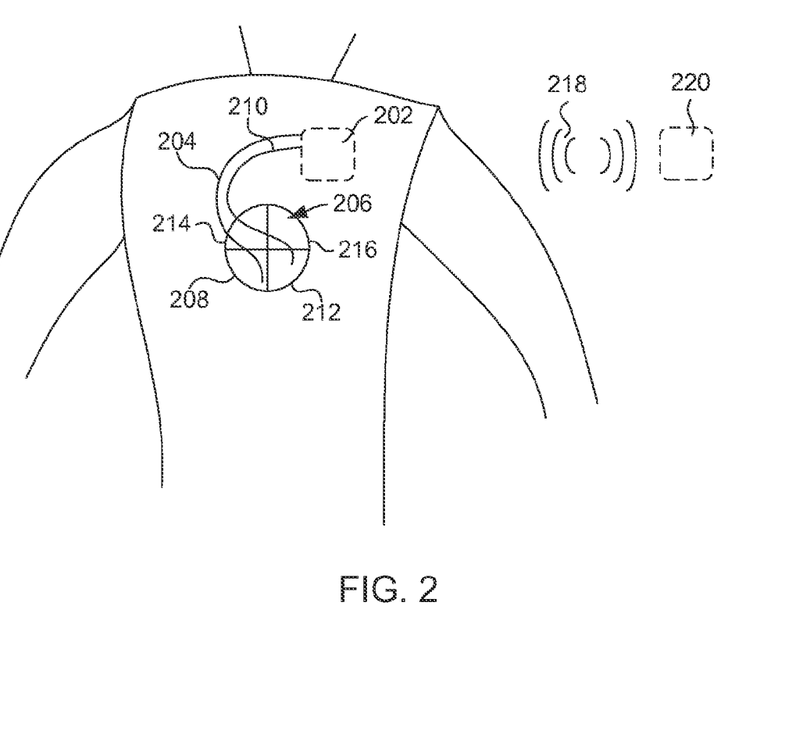
FIG. 2 is an implanted medical system including a battery that includes a fluorinated carbon framework defining open areas disposed along three axes, according to some examples.

FIG. 2 is an implanted medical system including a battery that includes a 3D framework, according to some examples. The system includes a cardiac rhythm management device 202 coupled to a first lead 204 to extend through the heart 206 to the right ventricle 208 to stimulate at least the right ventricle 208. The system also includes a second lead 210 to extend through the heart 206 to the left ventricle 212. In various examples, one or both of the first lead 204 and the second lead 210 include electrodes to sense intrinsic heart signals and to stimulate the heart. The first lead 204 is in direct contact (e.g., touching) with the right atrium 214 and the right ventricle 208 to sense and/or stimulate both of those tissue regions. The second lead 210 is in direct contact with the right atrium 216 and the right ventricle 212 to sense and/or stimulate both those tissue regions. The cardiac rhythm management device 202 uses the lead electrodes to deliver energy to the heart, between electrodes on the leads or between one or more lead electrodes and the cardiac rhythm management device 202. In some instances, the cardiac rhythm management device 202 is programmable and wirelessly communicates 218 programming information with a programmer 220. In certain examples, the programmer 220 wirelessly 218 charges an energy storage device of the cardiac rhythm management device 202. Other stimulation topologies, such as those that stimulate other portions of the body, additionally benefit from the devices and methods disclosed herein.

Figure 3A:
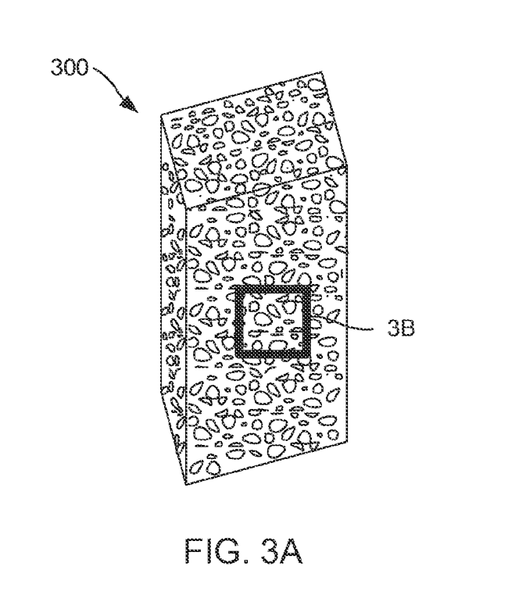
FIG. 3A is a perspective view of a fluorinated carbon framework defining open areas disposed along three axes, according to various examples.
Figure 3B:
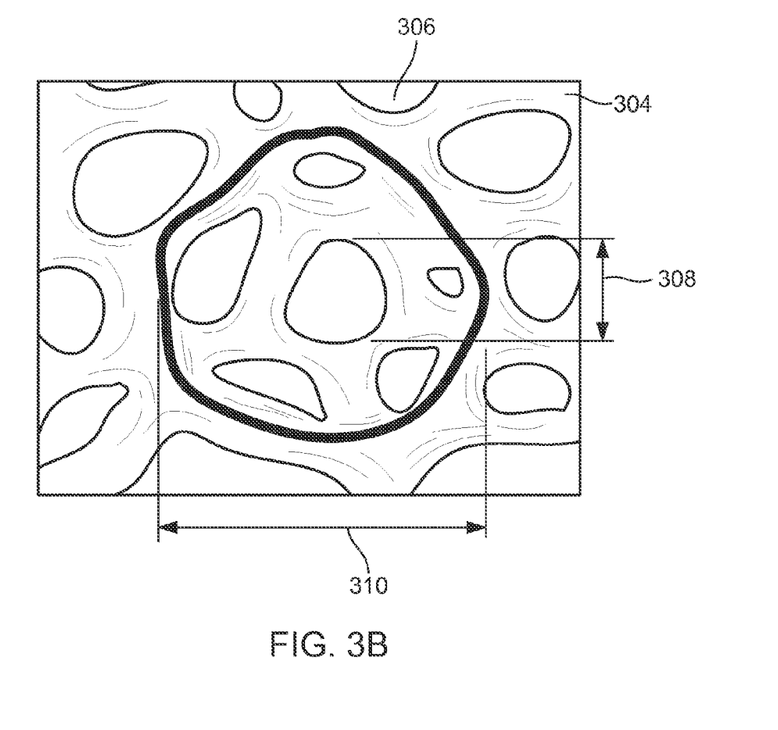
FIG. 3B is a close-up view of a fluorinated carbon framework defining open areas disposed along three axes such as the close-up view 3B depicted in FIG. 3A.

FIG. 3A is a perspective view of a 3D framework 300, according to various examples. FIG. 3B is a close-up view of a 3D framework such as the close-up view 3B depicted in FIG. 3A. The 3D framework pictured is porous and cathodic, but the present subject matter is not so limited. The 3D framework 300 is metallic in certain examples. As used herein, metallic materials are of, or relate to, being a metal, containing a metal or having properties of a metal. Metallic materials are formed of aluminum, titanium, stainless steel, other metals and combinations of those metals. In certain examples, the 3D framework 300 is continuous. A continuous metal demonstrates a regular distribution of grain boundaries, as opposed to a discontinuous metal with between grain boundaries, such as welded metals.

In some instances, the 3D framework is formed of foam. Some examples include metallic foams. In various examples, the 3D framework 300 is formed of metallic foam defining porous cells. In FIG. 3B, a cell 310 is defined by the framework 304. The cell, according to various examples, represents a bubble in the foam. At least some of the cells are open. Pores 306 provide fluid communication with other cells. Ionic conduction occurs through the pores, for example.

In various examples, the 3D framework 300 is pliable. For example, the 3D framework 300 can be compressed elastically, in certain examples. Some examples include a 3D framework compressed inelastically. As used herein, compressed relates to cells of foam pressed together and reduced in size or volume, such as by pressure. Compressed additionally means that the 3D framework 300 is flattened as though subjected to compression.

In certain examples, the 3D framework 300 is at least partially filled with an active material. In certain examples, the active material is disposed in slurry. Slurry, in general, is a thick suspension of solids in a liquid. In some instances, the active material is impregnated into the 3D framework 300.

In various examples, the active material includes, but is not limited to, carbon monofluoride, with a formula $CF_x$. In some examples, the current collector is substantially free of graphite. In certain examples, one or both of the 3D framework 300 and the active material are substantially free of carbon black. Examples of carbon black include, but are not limited to, acetylene black such as SHAWINIGAN BLACK, ("SAB"). SHAWINIGAN BLACK is a registered trademark of Chevron Phillips, headquartered in Houston, Tex.

In some instances, one or both of the 3D framework 300 and the slurry are compressed. In certain examples, a compressed 3D framework 300 including a compressed active material has a porosity of from around 45-55% porous. In various examples, the 3D framework provides an electrical network for electronic conduction, such as between an active material and a battery terminal. A benefit some instances provide is that the 3D framework reduces cathode swelling upon discharge and compressed powder spring-back.

In certain examples, a $CF_x$ cathode including a pressed pellet design without a 3D framework has a cathode porosity of around 58%. In certain examples, a 1.2 amp-hour battery has a predetermined volume and a cathode porosity of around 63%.

Certain examples include foam impregnated with $CF_x$ to have cathode porosity is around 52%. One of these examples has a formulation of around 11% aluminum, 2% polyvinylidene fluoride ("PVDF"), and 87% CFx. In at least some of the examples, a 1.2 amp-hour battery having a cathode specific capacity of 700 milliamp-hours per gram occupies around 3.46 cubic centimeters.

In some examples, a $CF_x$ cathode including a coated foil design without a 3D framework has a cathode porosity of around 73%. In some of these examples, the cathode delaminates undesirably. Some instances have a formulation of 3% graphite, 2% SAB, 7% PVDF and 88% $CF_x$, coated on aluminum foil. In certain examples, a 2.0 amp-hour battery has a volume of 9.3 cubic centimeters. Some of these examples comprise seven cathode layers in a stack of electrodes.

Some examples include an electrode with a porosity of from around 30-55% porous. Certain examples include foam impregnated with $CF_x$ that has a cathode porosity around 52%. Some of these examples have a formulation of around 11% aluminum, 2% polyvinylidene fluoride ("PVDF"), and 87% $CF_x$. In at least certain examples that include $CF_x$ in a 3D framework, a 2.0 amp-hour battery having a cathode specific capacity of 625 milliamp-hours per gram occupies around 6.7 cubic centimeters. Some of these examples comprise cathode layers in a stack of electrodes.

In one example, a 1.2 amp hour $MnO_2$ battery having a gravimetric capacity of 308 milliamp hours per gram has a volumetric capacitor of 1540 milliamp hours per cc has a volume of at least 3.91 cubic centimeters. A 2.0 amp hour battery having a similar specific and volumetric capacity has a volume of around 8.64 cubic centimeters.

Contrast $CF_x$ battery examples including a 3D framework. Some instances have a cathode specific capacity of 860 milliamp hours per gram has a volumetric capacity of 2322 milliamp hours per cc has a volume of less than 3.46 cubic centimeters. A 2.0 amp hour battery having a similar gravimetric and volumetric capacity has a volume of less than 6.0 cubic centimeters.

Figure 4A:
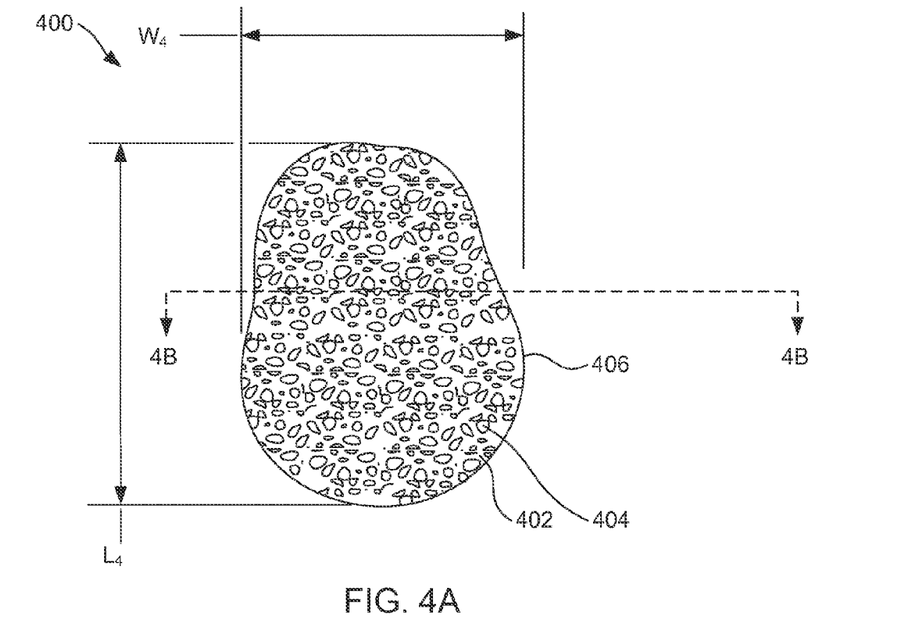
FIG. 4A is a plan view of a fluorinated carbon framework defining open areas disposed along three axes, according to various examples.
Figure 4B:
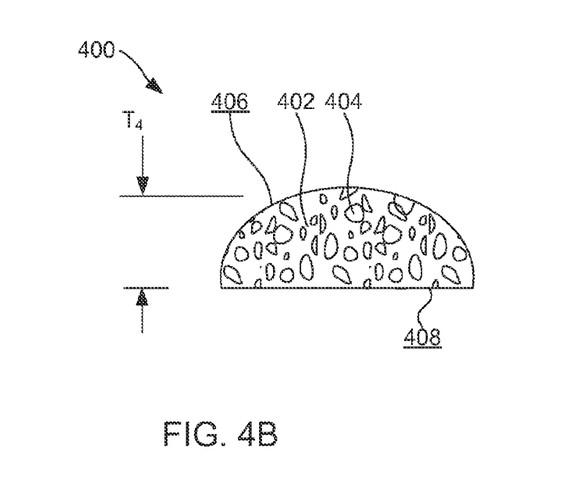
FIG. 4B is a cross section taken along line 4B-4B in FIG. 4A.

FIG. 4A is a plan view of a 3D framework 400, according to various examples. FIG. 4B is a cross section taken along line 4B-4B in FIG. 4A. The electrode 400 is impregnated with slurry and compressed in these examples. The electrode defines a plurality of pores 404. In certain examples, the electrode has an electrode shape 406 that is selected to at least partially mate a battery case shape. In some instances, the electrode 400 is cut, such as by routing or another cutting operation. In some examples, the electrode has a flat surface 408. In certain examples, additional electrodes are stacked onto the flat surface 408. An electrode stack includes a number of electrodes, each including at least one major face that faces a major face of another electrode. In some instances, a plurality of electrodes are disposed in a stack and interconnected with one another. Interconnection is via a conductive interconnect, in some examples. Examples of an interconnect include, but are not limited to, a weld busbar, rivet, metal spray and the like.

In various examples, the width $W_4$ and the thickness $T_4$ are selected such that the electrode 400 conforms to or mates with a selected battery case shape. Examples include a 3D framework 402 that is connected to a conductor. In certain examples, the electrode 400 is coupled to a conductor. A conductor is welded to the 3D framework 402 such that it is electrically and physically coupled to the 3D framework 402, in certain examples. In various examples, a device housing has a form factor, and the battery case is shaped to at least partially conform to the form factor.

Figure 5A:
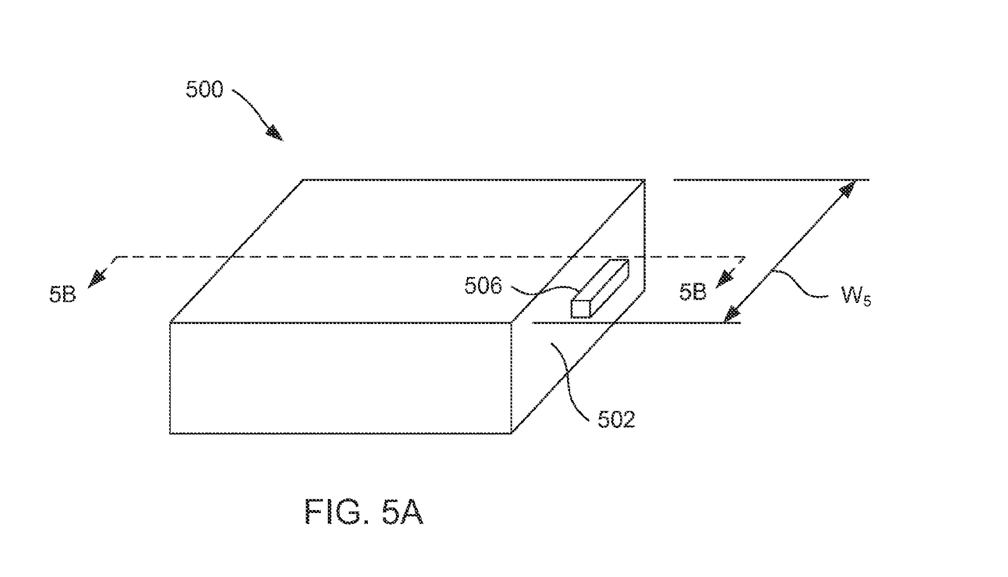
FIG. 5A is a perspective view of an electrode, according to some examples.
Figure 5B:
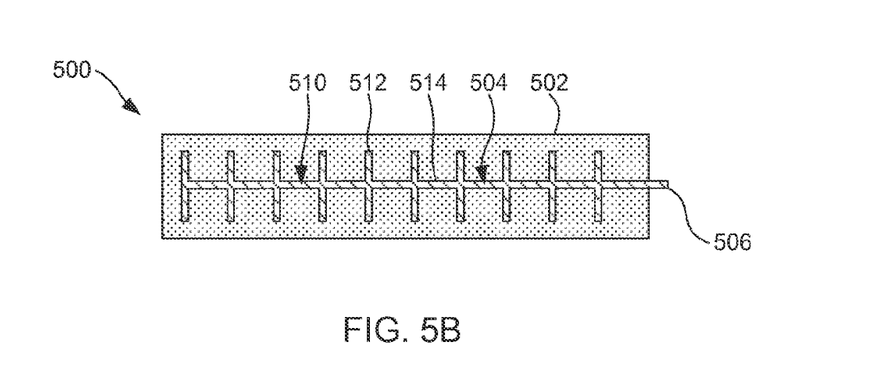
FIG. 5B is a cross section taken along line 5B-5B.

FIG. 5A is a perspective view of an electrode 500, according to some examples. FIG. 5B is a cross section taken along line 5B-5B. Active material 502 is disposed onto an internal portion 504 of a current collector 510. A connection member 506 extends outside the active material 502. In some instances, the internal portion 504 of the current collector spans the entire width of the active material 502, but examples in which it spans less than the entire width $W_5$ are additionally possible. In certain examples, further currently collector material, such as metallic foam, is coupled to the internal portion 504 such as by welding.

As shown, the internal portion 504 comprises fins 512 extending away from an internal support 514. In some instances, the fins 512 are plate shaped and linear. In certain examples, they're curvilinear. In certain examples, the internal support 514 is plate shaped. In some instances, it is a plate defining many openings, such as circular openings. In some examples, it is a grid. In additional examples, it is a web. In various examples, the fins 512 are orthogonal to the internal support 514.

Figure 6A:
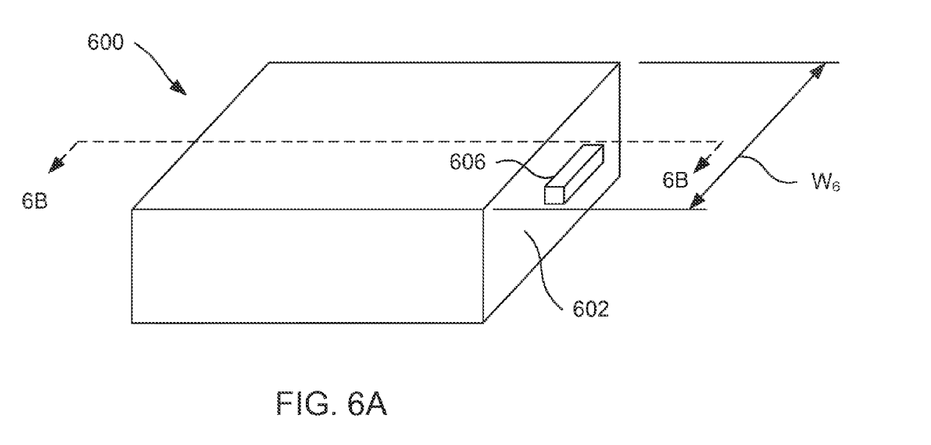
FIG. 6A is a perspective view of an electrode, according to some examples.
Figure 6B:
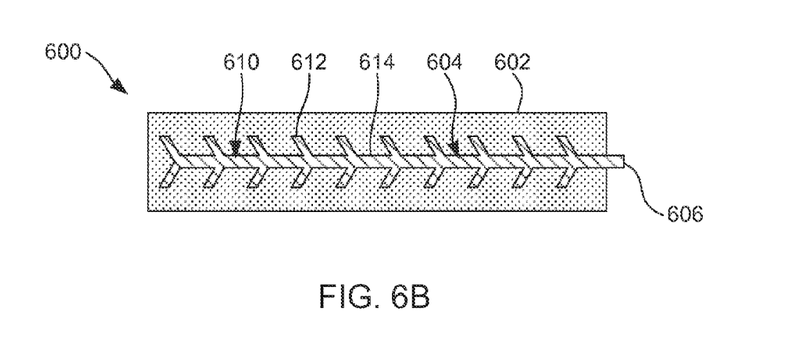
FIG. 6B is a cross section taken along line 6B-6B.

FIG. 6A is a perspective view of an electrode 600, according to certain examples. FIG. 6B is a cross section taken along line 6B-6B. Active material 602 is disposed onto an internal portion 604 of a current collector 610. A connection member 606 extends outside the active material 602. In some examples, the internal portion 604 of the current collector spans the entire width of the active material 602, but examples in which it spans less than the entire width $W_6$ are additionally possible. In some instances, further currently collector material, such as metallic foam, is coupled to the internal portion 604 such as by welding.

As shown, the internal portion 604 comprises canted fins 612 extending away from an internal support 614. In certain examples, the canted fins 612 are plate shaped and linear. In certain examples, they're curvilinear. In some instances, the internal support 614 is plate shaped. In certain examples, it is a plate defining many openings, such as circular openings. In some instances, it is a grid.

Figure 7A:
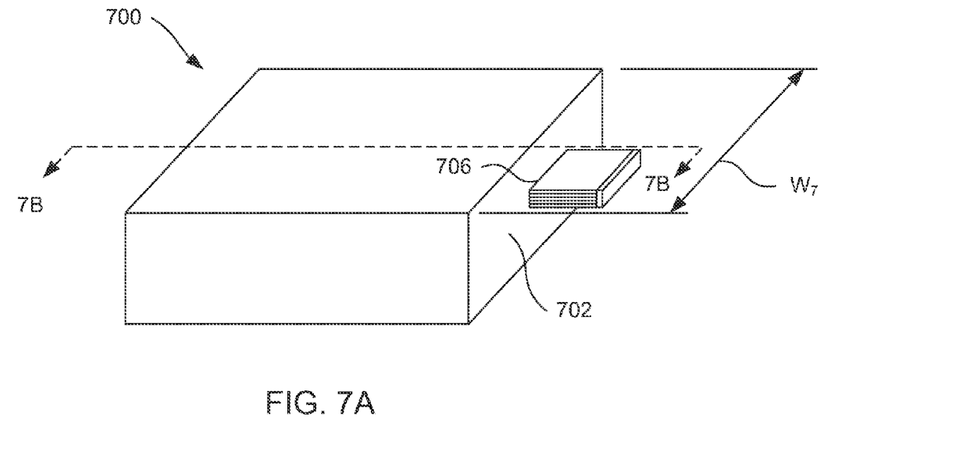
FIG. 7A is a perspective view of an electrode, according to some examples.
Figure 7B:
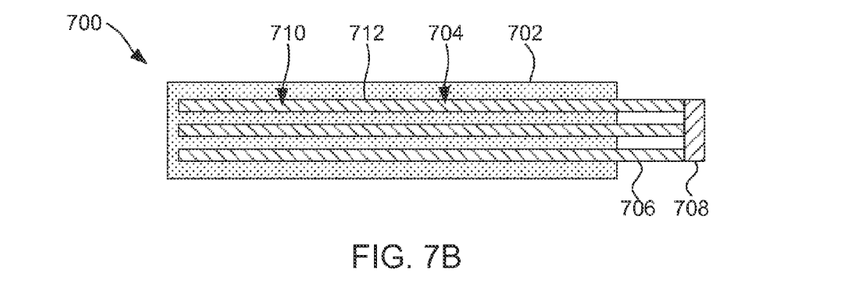
FIG. 7B is a cross section taken along line 7B-7B.

FIG. 7A is a perspective view of an electrode 700, according to some examples. FIG. 7B is a cross section taken along line 7B-7B. Active material 702 is disposed onto an internal portion 704 of a current collector 710. A connection member 706 extends outside the active material 702. In certain examples, the internal portion 704 of the current collector spans the entire width of the active material 702, but examples in which it spans less than the entire width $W_7$ are additionally possible. In certain examples, further currently collector material, such as metallic foam, is coupled to the internal portion 704 such as by welding.

As shown, the internal portion 704 comprises layers 712 extending away from an interconnect 708. In some instances, the layers 712 are plate shaped and linear. In certain examples the layers 712 are parallel to one another. In some examples, a spacer spaces the layers apart. Accordingly, in some instances, the layers 712 are in a spaced-apart stack. In certain examples, they're curvilinear. In some instances, one or more of the layers 712 include a plate defining many openings, such as circular openings. In certain examples, the layers 712 include a grid.

Figure 8A:
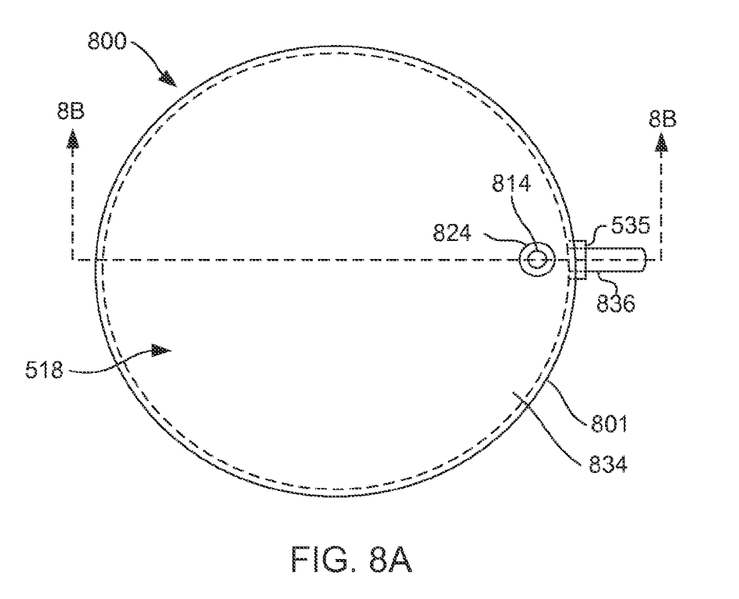
FIG. 8A is a plan view of a battery, according to various examples.
Figure 8B:
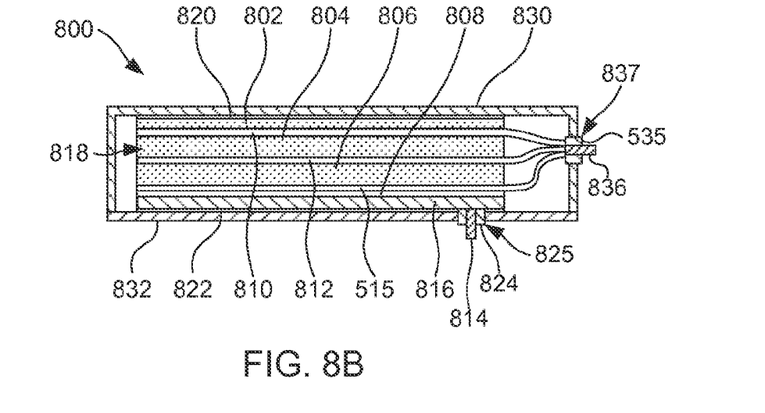
FIG. 8B is a cross section taken along the line 8B-8B in FIG. 8A.

FIG. 8A is a plan view of a battery, according to various examples. FIG. 8B is a cross section taken along the line 8B-8B in FIG. 8A. Various examples include a battery stack 818 disposed in a battery case 801. The battery case 801, in various examples, includes a dish shaped portion 830 and a lid 832, with the lid sealed to the dish shaped portion 830, but the present subject matter is not so limited.

In various examples, the battery stack 818 includes a plurality of electrodes and separator. For example, a first separator 820 is disposed between the case 801 and a first electrode including a 3D framework 802 to physically separate the electrode including a 3D framework 802 from the case 801. In certain examples, the electrode including a 3D framework 802 is coupled to a conductor 810. Some instances include a second electrode including a 3D framework 804 coupled to a conductor 812. Some examples include a third electrode including a 3D framework 806 coupled to a conductor 815. In certain examples, the first, second and third electrodes abut and are in electrical communication with one another. In additional examples, the first, second and third electrodes abut the battery case 801. In some examples, the first, second and third electrodes are cathodic. In various examples, the stack 818 is a stack of compressed electrodes, each adapted to stack into the stack. An electrode adapted for stacking, in some instances, is prepared in pelletized before stacking. In certain examples, electrodes in a stack are compressed after stacking.

In certain examples, the first, second and third electrodes are electrically coupled via an interconnection between the first conductor 810, the second conductor 812 and the third conductor 815. Interconnection between the first conductor 810, the second conductor 812 and the third conductor 815 is via a conductive interconnect. Each of the conductors is electrically coupled to a respective 3D framework via welding and the like. In some instances, a conductor is formed of a metallic spray. Certain examples include a metallic ribbon coupled to the 3D framework.

In various examples, a feedthrough 837 including an electrical insulator 835 and a terminal 836 is disposed through the dish shaped portion 830 and placed into connection with the first conductor 810, the second conductor 812 and the third conductor 815 such as by welding.

Various examples additionally include a further electrode 816. In various examples, one or more separators 808 separate the further electrode 816 from additional electrodes, such as the electrode including conductor 815. In additional examples, a separator 822 separates the further electrode 816 from the case 801 such as by separating the further electrode 816 from the lid 832.

In various examples, the first, second and third electrodes are stacked into the dish shaped portion 830. Separator is stacked onto the third electrode, and a further electrode 816 is stacked into the dish shaped portion 830. In various examples, a lid 832 is fixed to the dish shaped portion, with a feedthrough 825 including an electrical insulator 824 and a terminal 814 is disposed through the lid 832 and placed into connection with the further electrode 816 such as by welding. In some examples, the further electrode 816 is welded to the feedthrough prior to fastening the lid 832 to the dish shaped portion 830.

Figure 9:
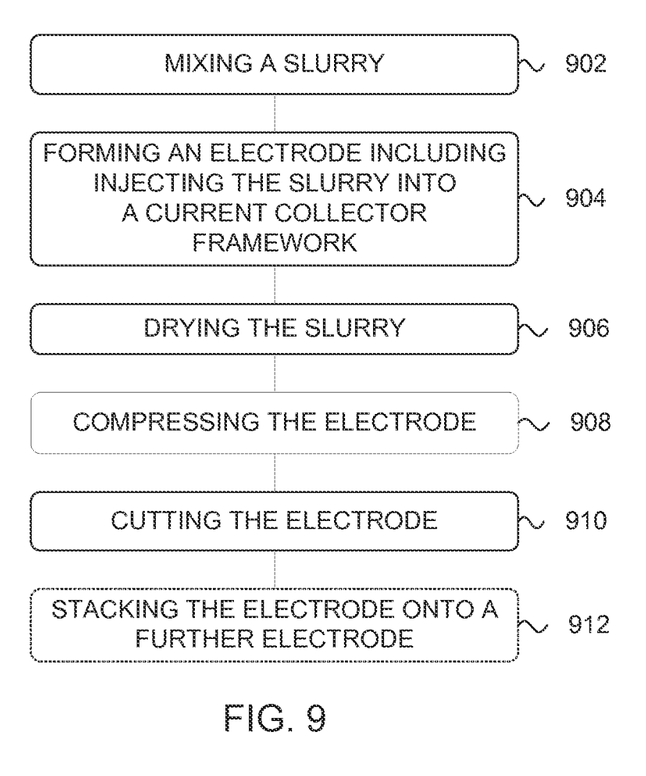
FIG. 9 is a method of making a battery including a fluorinated carbon framework defining open areas disposed along three axes, according to some examples.

FIG. 9 is a method of making a battery including a 3D framework, according to certain examples. At 902, the method includes mixing slurry. In some examples, mixing a slurry includes combining an electrochemically active component with carbon. In certain examples, it also includes mixing in a binder. In some examples, it also includes mixing in a solvent. The slurry is randomized or mixed with a planetary type mixer, in some examples. At 904, the method includes forming an electrode including injecting the slurry into a current collector framework. At 906, the method includes drying the slurry. At 908, the method includes compressing the electrode. Optionally, this includes compressing the current collector framework after slurry is injected. At 910, the method includes cutting the electrode. Optionally, the electrode is cut after slurry is injected into the current collector framework. At 912, the method optionally includes stacking the electrode onto a further electrode.

Figure 10:
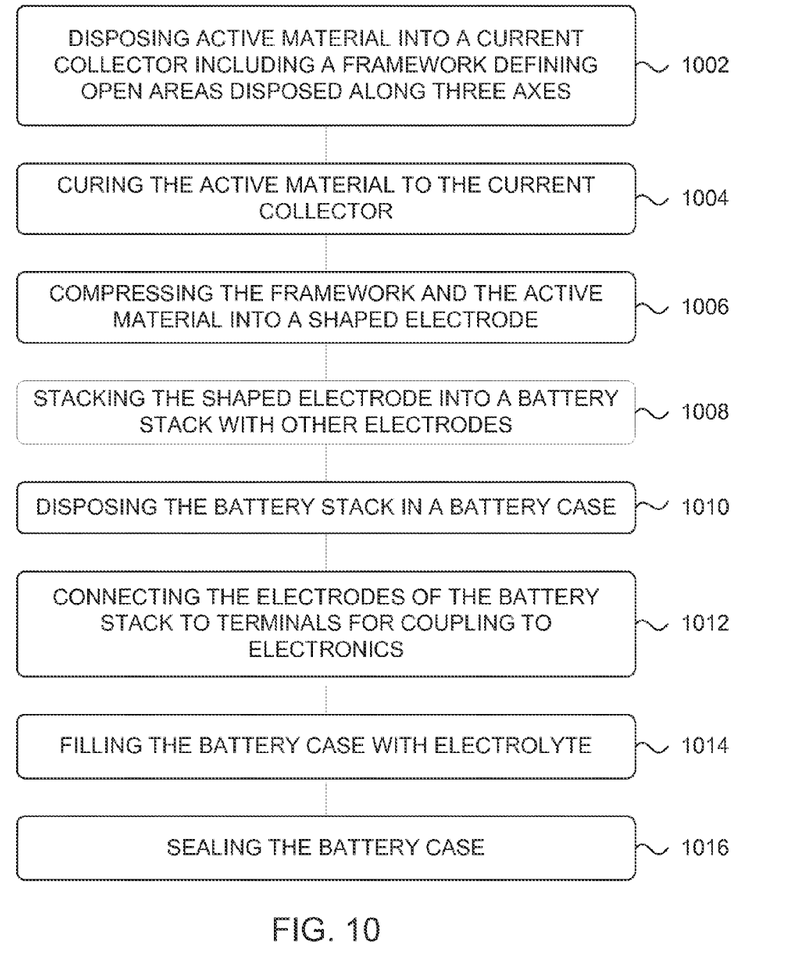
FIG. 10 is a method of making a battery including a fluorinated carbon framework defining open areas disposed along three axes, according to some examples.

FIG. 10 is a method of making a battery including a 3D framework, according to some instances. At 1002, the method includes disposing active material into a current collector including a 3D framework. At 1004, the method includes curing the active material to the current collector. At 1006, the method includes compressing the 3D framework and active material into a shaped electrode. At 1008, the method includes stacking the shaped electrode into a battery stack with other electrodes. At 1010, the method includes disposing the battery stack in a battery case. At 1012, the method includes connecting the electrodes of the battery stack to terminals for coupling to electronics. At 1014, the method includes filling the battery case with electrolyte. At 1016, the method includes sealing the battery case.

Figure 11:
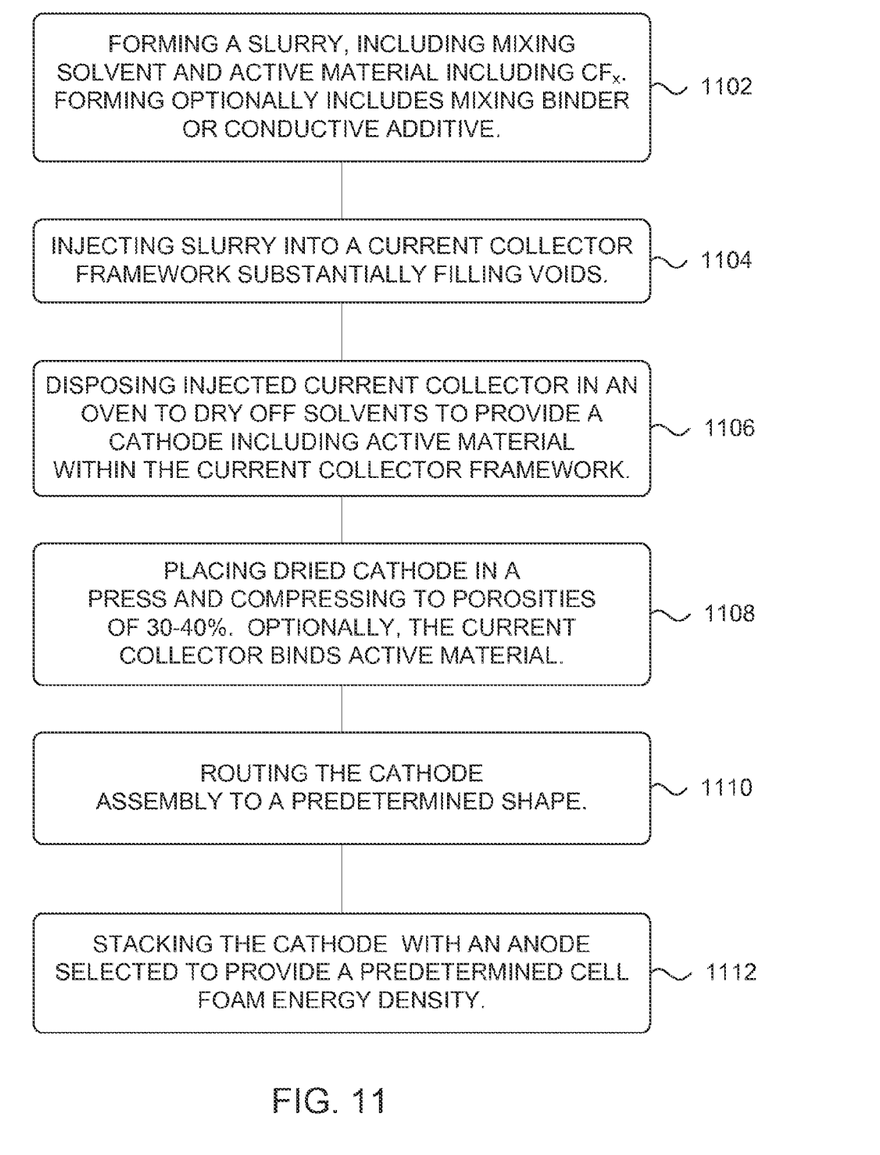
FIG. 11 is a method of making a battery including a fluorinated carbon framework defining open areas disposed along three axes, according to some examples.

FIG. 11 is a method of making a battery including a 3D framework, according to certain examples. At 1102, the method includes forming a slurry, including mixing solvent and active material including CFx. Forming optionally includes mixing binder or conductive additive. At 1104, the method includes Injecting slurry into a current collector framework substantially filling voids. At 1106, the method includes Disposing Injected current collector in an oven to dry off solvents to provide a cathode including active material within the current collector framework. At 1108, the method includes placing dried cathode in a press and compressing to porosities of 30-40%. Optionally, the current collector binds active material. At 1110, the method includes routing the cathode assembly to a predetermined shape. At 1112, the method includes Stacking the cathode with an anode selected to provide a predetermined cell foam energy density.

Aspects of the methods of FIGS. 6, 7 and 11 can be used in combination. Some methods additionally include forming the 3D framework out of metallic foam. Some methods include forming the active material by mixing carbon monoflouride into slurry with binder and conductive additive. In some methods, disposing active material includes injecting the active material into the 3D framework. In some methods, curing the active material includes baking the active material in an oven. In some methods, compressing the 3D framework includes compressing to a porosity of from around 30% to 40%. Some methods include cutting an excised electrode from the shaped electrode. Some methods include stacking the other electrodes into the stack such that the stack has a predetermined energy density. In some methods, a stack is formed by a process comprising stacking an uncompressed electrode and a further uncompressed electrode into an uncompressed stack, and stacking the uncompressed stack.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus, comprising:
 a battery case sealed to retain electrolyte;
 a pelletized first electrode disposed in the battery case, the first electrode comprising a current collector including an electrically-conductive, metal framework defining open areas disposed along three axes with active material disposed in the open areas of the metal framework, wherein the active material comprising carbon monoflouride, with a formula CFx;
 a conductor electrically coupled to the first electrode and sealingly extending through the battery case to a terminal disposed on an exterior of the battery case;
 a pelletized second electrode disposed in the battery case;
 a separator disposed between the first electrode and the second electrode; and
 a second terminal disposed on the exterior of the battery case and in electrical communication with the second electrode.

2. The apparatus of claim 1, wherein the framework is formed of a compressed metallic foam.

3. The apparatus of claim 2, wherein the metallic foam is formed of at least one of the group comprising aluminum, titanium and stainless steel.

4. The apparatus of claim 1, wherein the first electrode has a porosity of from around 30-55% porous.

5. The apparatus of claim 1, wherein the first and second electrodes are disposed in a stack of electrodes.

6. The apparatus of claim 5, wherein the second electrode includes a current collector formed of a compressed metal framework that is electrically conductive.

7. The apparatus of claim 6, wherein the stack is formed by a process comprising stacking an uncompressed electrode and a further uncompressed electrode into an uncompressed stack, and stacking the uncompressed stack.

8. The apparatus of claim 6, wherein the stack of electrodes is a stack of compressed electrodes.

9. The apparatus of claim 1, further comprising:
 a hermetically sealed device housing;
 a battery disposed in the hermetically sealed device housing, the battery comprising:
 the battery case sealed to retain electrolyte;
 the first electrode disposed in the battery case;
 the conductor;
 the second electrode disposed in the battery case;
 the separator;
 the second terminal disposed on the exterior of the battery case and electrical communication with the further electrode; and
 an electronic cardiac rhythm management circuit coupled to the battery and adapted to discharge the battery to provide a therapeutic pulse.

10. The apparatus of claim 9, wherein the device housing has a form factor, and the battery case is shaped to at least partially conform to the form factor.

11. The apparatus of claim 10, wherein the battery case has a case shape, and the first electrode has an electrode form factor shaped to mate the case shape.

12. The apparatus of claim 1, wherein the framework includes a three-dimensional framework selected from the group consisting of: foam, fabric, thatch, braid, scaffolding, skeleton, fins, and tendrils.

13. The apparatus of claim 1, wherein the framework includes a three-dimensional cellular volume.

14. The apparatus of claim 13, wherein at least some of the plurality of cells are open cells.

15. The apparatus of claim 1, wherein the framework is configured to be inelastically compressed to form the pelletized first electrode.

16. An apparatus, comprising:
 a battery case sealed to retain electrolyte, wherein the battery case has a case shape;
 a pelletized first electrode disposed in the battery case, the first electrode comprising a current collector, the current collector having an electrically-conductive, metal framework that defines open areas disposed along three axes, the metal framework including a three-dimensional cellular volume, wherein active material is disposed in the open areas of the metal framework, wherein the active material comprising carbon monofluoride with a formula CFx, and wherein the pelletized first electrode has a form factor shaped to mate the case shape, and the metal framework is configured to be compressed into the form factor;

a conductor electrically coupled to the electrode and sealingly extending through the battery case to a terminal disposed on an exterior of the battery case;

a pelletized second electrode disposed in the battery case;

a separator disposed between the first electrode and the second electrode; and a second terminal disposed on the exterior of the battery case and in electrical communication with the second electrode.

17. The apparatus of claim 16, wherein at least some of the plurality of cells are open cells.

18. The apparatus of claim 16, wherein the metal framework is configured to be compressed into the form factor of the pelletized first electrode.

19. The apparatus of claim 16, wherein the metal framework includes a metallic foam.

* * * * *